United States Patent [19]

Eisenmenger

[11] Patent Number: 4,807,627
[45] Date of Patent: Feb. 28, 1989

[54] CONTACTLESS COMMINUTION OF CONCREMENTS

[76] Inventor: Wolfgang Eisenmenger, Landhausstrasse 7, 7140 Ludwigsburg, Fed. Rep. of Germany

[21] Appl. No.: 884,353

[22] Filed: Jul. 11, 1986

[30] Foreign Application Priority Data

Jul. 18, 1985 [DE] Fed. Rep. of Germany ....... 3525641
Jul. 23, 1985 [DE] Fed. Rep. of Germany ... 8521196[U]

[51] Int. Cl.$^4$ ............................................. A61B 17/00
[52] U.S. Cl. .................................................... 128/328
[58] Field of Search ..................... 128/328, 24 A, 660; 604/22; 310/322, 334, 369, 371; 73/643, 642; 367/150

[56] References Cited

U.S. PATENT DOCUMENTS

| 3,086,195 | 4/1963 | Holliday | 310/334 |
| 3,626,218 | 12/1971 | Shriver | 128/328 |
| 3,735,764 | 5/1973 | Balev et al. | 128/24 A |
| 4,182,173 | 1/1980 | Papadofrongaskis et al. | 128/663 |
| 4,311,147 | 1/1982 | Häusler | 128/328 |
| 4,315,514 | 2/1982 | Drewes et al. | 128/24 A |
| 4,368,401 | 1/1983 | Martin et al. | 310/322 |
| 4,526,168 | 7/1985 | Hassler et al. | 128/328 |
| 4,530,363 | 7/1985 | Brisken | 128/663 |

FOREIGN PATENT DOCUMENTS 3033598 4/1982 Fed. Rep. of Germany ... 128/24 A
3312014 10/1984 Fed. Rep. of Germany ...... 128/328

OTHER PUBLICATIONS

Lehmann, J. F., Therapic Heat and Cold, 3rd Edition, 1982, pp. 365 to 377.
Choussey, Extracorporeal Shock Wave Lithotripsy, p. 4, 1978.

Primary Examiner—C. Fred Rosenbaum
Assistant Examiner—Mark F. Colosimo
Attorney, Agent, or Firm—Ralf H. Siegemund

[57] ABSTRACT

Contactfree comminution of concrements in the body of a living being by means of focused shock waves, there being an axis on which a concrement is located; the improvement relates to controlling the production of shock waves (a) spherically such that the shock wave pressure amplitude decreases with radial distance from said axis and (b) temporally such that the amplitudes rise steeply at first and decay relatively slowly after having passed through a maximum.

29 Claims, 5 Drawing Sheets

CONTACTLESS COMMINUTION OF CONCREMENTS

BACKGROUND OF THE INVENTION

The present invention relates to the contactless comminution of concrements in the body of a living being by means of shock waves which are focused onto the concrement.

A device of the type to which the invention pertains is, for example, shown in German printed patent application No. 3,312,014. A further improvement is disclosed in my copending patent application Ser. No. 802,720, filed Nov. 27, 1985. Among other features an electrical conductor arrangement is disclosed therein, having inductive properties owing to the configuration as a spirally shaped coil or as a coil wound from a flat ribbon. The coil is configured from an overall point of view, to have the shape of a spherical calotta. Upon feeding an electrical pulse into this coil, for example, on account of a capacitor discharge through a spark gap included in the circuit will produce a spark, so that a current pulse flows through the coil. A metal membrane faces the coil, but is separated therefrom by a thin electrical insulated layer and a current in opposite direction is induced resulting in a repulsion of the membrane from the coil. Since the membrane is in physical contact with an acoustic transmitting medium, shock waves are produced therein, and owing to the calotta shaped configuration of the membrane, these shock waves are focused. In order to avoid diffraction and reflection as it may occur at the housing part facing the membrane, I proposed in my co-pending application, to configure the zone into which the membrane emits the shock wave to be a truncated cavity filled with the transmission medium. Decisive here is a conical boundary of that medium delineating the focussing direction of the outermost beam portion.

Other known devices for the comminution of concrements operate with submerged spark gaps for the production of shock waves in the one focal point of an ellipsoid focusing the shock waves into the second focal point being situated to coincide with the concrement to be comminuted. Other devices for the generation of shock waves operate, for example, on the basis of piezoelectric effects or are constructed as magnetostrictive elements.

All these known devices require focusing of the shock waves but they all are constructed so that for physical reasons a negative pressure pulse wave cannot be completely avoided. Should these pressure drop pulses exceed a particular strength then the commensurate fucusing effect of this negative pressure pulse may also be particularly effective in the tissue of the living being be traversed and may lead to cavitation, i.e. to microscopic leasures and outright injuries to the tissue.

DESCRIPTION OF THE INVENTION

It is an object of the present invention to provide a new and improved method and equipment for the comminution of concrements in living beings by means of focused shock waves which avoids damage and injury to tissue on account of negative pressure pulses.

It is a feature of the present invention to avoid the formation of edge and fringe diffraction waves of the focusing system which are the underlying cause for the formation of a secondary focused negative pressure pulse.

In accordance with the preferred embodiment of the present invention, it is suggested to attain the objective by contouring the pressure amplitude of the shock wave such that locally its strength is reduced in radial outer direction. This reduction of the sharpness of the pressure drop at the edge of the shock waves entails a significant weakening of fringe diffractive waves and that, in turn, avoids the formation of negative pressure pulses to which tissue damage has been contributed. Moreover, the lowering of the amplitude of the shock waves towards the edges is, in fact, a contributing factor for improving the contour and genesis of the shock waves proper. In a particularly advantageous way of practicing the invention, it is suggested to rather steeply increase the pressure amplitude of the shock wave followed by a more gradual reduction. In other words, the shock waves are given a triangular amplitude modulation so that negative pressure pulses are also avoided. This triangular contour in terms of time pressure relationship enhances, on the other hand, the pressure amplitude proper while on the other hand the amplitude reduction in radial outer direction is enhanced further.

A particular advantage to control the pressure amplitude is that the excitation density or energization strength of the shock waves or both, are individually, controlled as to their spatial distribution. It is not important how the shock wave is actually produced, in other words, the invention can be practiced regardless of the particular generation of a shock wave be it by membrane-coil repulsion, piezoelectric energization, magnetostrictive energization or underwater or submerged spark gap discharge and ellipsoidal focusing. In all these systems either the energization density or the energization strength or both can be controlled in one form or another, particularly in letting the intensity decrease from a point on the axis in radial direction.

In accordance with the invention certain equipment is proposed which provides locally a lowering of the shock wave and its propagation in radial direction, possibly under inclusion of temporal increase followed by a more gradual lowering of the pressure amplitude, i.e. a steep pulse, of the respective shock wave. Again, coil-membrane energization, piezoelectric energization, magnetostrictive energization, or underwater spark gap plus focusing operation may be used.

A particularly advantageous configuration of practicing the invention includes a metal membrane carrying on one side a thin electrical insulated layer by means of which a flat, e.g. printed on, conductor-coil is separated while the other side of the membrane works against an acoustic transmission medium. The overall arrangement is constructed in a spherical calotta configuration and will be energized in its entirety by an electric pulse whose strength and duration is controlled. In accordance with the objective of the invention this arrangement and device must not produce a negative pressure pulse so as to avoid damage to tissue. This is attained, for example, by lowering the winding density of the electrical conductor as mounted; in addition or alternatively, the cross-section of the conductor increases in radially outward direction. Still alternatively or additionally, individual windings or coil loops can be provided following that rule in that the windings are more closely spaced near the calotta center than near the edge. A combination of the spatial distribution and temporal pulse control inceresases the reduction of the sharp pressure drop of the edge near waves and thereby reduces the danger to tissue further. This smooth reduction in amplitude in radial direction is to be over and beyond any sharp decrease in shock wave excitation amplitude, e.g. on account of a short distance radial decrease in membrane deflection. It is to be emphasized that in contrast to a sharp radial amplitude decay as usually observed at the rim of the aperture of so far known focussing systems for shock waves the present invention uses an artificially and smoothly decaying radial amplitude distribution in order to minimize the amplitude of the negative pressure tail of the positive pressure shock wave causing the kidney stone destruction. Thus avoiding the negative pressure tail is equivalent to avoiding cavitation and in turn leisures of especially the kidney tissue itself.

The above-mentioned German printed patent application No. 3,212,014 discloses a device in which a metal membrane adjoins a spherical calotta shaped conductor configuration. This conductor configuration is configured as spirally wound wire coil. Internal connection leads to the coil from the center as well as from a point along the outer edge. This kind of a membrane coil arrangement is feasable in principle but can be manufactured only with great difficulties and requires very accurate and highly skilled manual labor. Particularly the rather strong bending of the wire in the center often leads to damage of the thin insulation of the coil wire itself, and that, in turn, increases the danger of insulation breakthrough, i.e. of short-circuit, which, in turn, of course, leads to uselessness of such an arrangement. Also the rather strong load on the metal membrane during operation results occassionally to fatigue fractures particularly in the central membrane area which again renders the entire coil-membrane arrangement useless. In the past, therefore, it was not really possible to provide coil membrane arrangements of a long use life. In furtherance of the invention, it is therefore another objective to increase the use life of such a membrane-coil arrangement. This objective is attained by providing one terminal for the conductor off the center so that in the winding center of the coil on account of any inherently large curvature sharp edges or even corners are avoided so that the insulating lacquer of the conductor will not longer be damaged during manufacture. The spacing of the inner terminal of the coil from the center depends to some extent on the cross-section of the wire being used, and should be optimized through empirical tests.

In furtherance of the invention the membrane should be provided with corrugations which maybe annually, radially, or spirally oriented. This corrugation pattern offers the advantage that the membrane is better equipped towards expansion and that, in turn, avoids fatigue, rupture of the membrane.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantages thereof will be better understood from the following description taken in connection with the accompanying drawings, in which:

Proceeding now to the detailed description of the drawings, FIG. 1 illustrates a casing or housing 1 which is comprised of two housing or casing parts 1a and 1b. The part 1b is hollow and filled with a liquid, for example, water. The cavity 2 of part 1b is covered by means of an elastic or resilient cover element 3 which is tied and sealingly connected to the part 1b through a fastening ring 4 and under utilization of screws or bolts 5. The cover 3 has a buffer-like central projection 3a which sealingly abuts either the skin 6 of a patient 19 directly or a coupling liquid having an interface as interposed between the equipment and the body of the patient, and the outer face of the projection 3a abuts that interface. The cover 3 is made, for example, of a rubber-elastic material.

Figure 1:
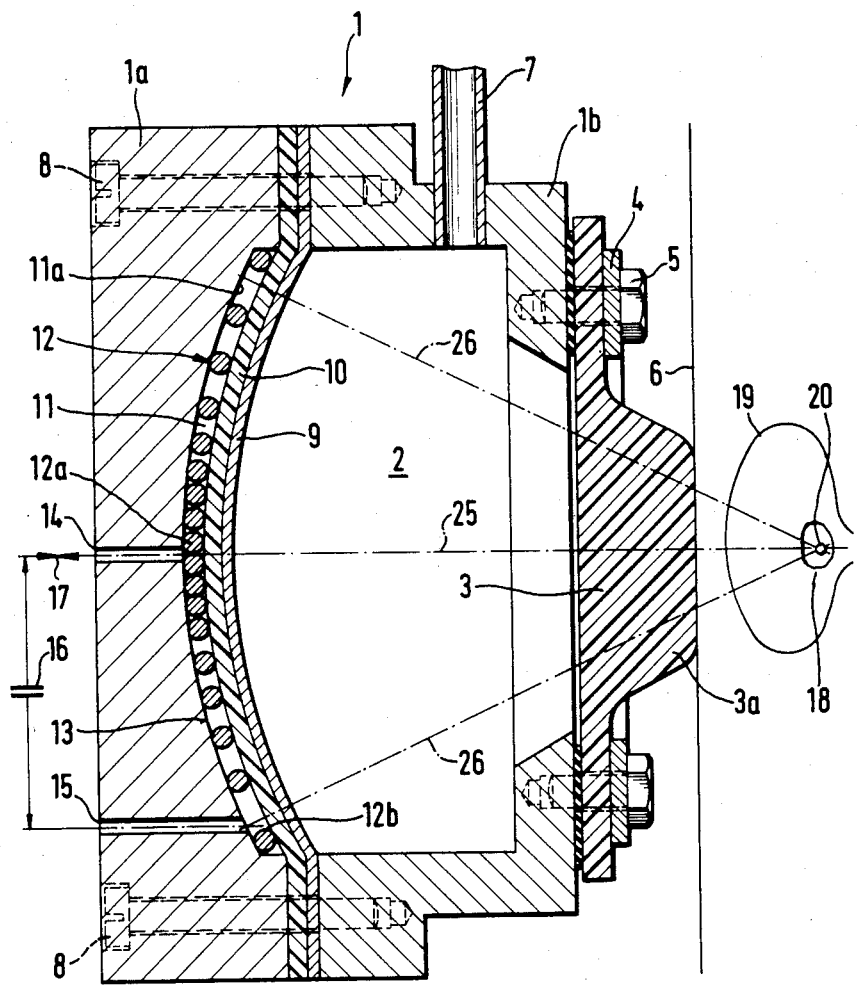
FIG. 1 is a somewhat schematic showing of a crossection of a device for practicing the preferred embodiment of the present invention in accordance with the best mode thereof.

The housing or casing parts 1a and 1b are bolted together by means of screws 8. Herein then a metal membrane 9 as well as an electrically insulating foil 10 are clamped and tensioned between the two housing parts 1a and 1b. These parts 9 and 10 will be forced under pressure in the cavity 2, tightly against a spherical calotta shaped surface 13 of the housing part 1a particularly. Housing part 1a provided with a recess 11 is filled in this particular example by a conductor arrangement 12.

The cavity 2 within the casing part 1b is connected through an inlet connection 7 with a pressure source (not shown). Pressurized liquid is forced into the cavity 2 in this manner and insures that the cavity 2 is always under a certain static excess pressure. The pressure differential as between the interior of the cavity and the external world is decisive. However, one could provide in a particular low pressure the space 11 ahead of the calotta shaped surface 11a and behind the membrane 9. That pressure is low in comparison to whatever pressure is applied to the cavity 2. In either case, the membrane 9 is firmly forced against the conductor arrangement 12 which, in turn, is forced thereby against the spherically shaped bottom 13 of recess 11.

The conductor arrangement 12 is constructed as a spirally looped coil, the coil being made of an electrically conducting wire, for example, a copper wire. The coil may be established at the beginning from a starting point 12a situated in the axis of spherical calotta 11, and spirally the individual loops are placed onto the inner spherical calotta shaped surface 13 of the recess 11 in housing part 1a, until an outermost loop 12b obtains. The thus resulting conductor arrangement 12 is basically a flat spirally shaped coil whose both ends 12a and 12b are connected to terminals 14 and 15 which, in turn, are connected to a capacitor 16 and a spark gap 17.

This source of energy 16, 17 provides an electric current pulse of short duration whenever the capacitor 16 discharges on account of a spark produced in gap 17. As a consequence, a current of short duration flows through the coil. Subsequently, the capacitor 16 is permitted to recharge. On discharge of the capacitor 16 the current flowing through coil 12 induces in the metal membrane 9 opposing currents such that the resulting magnetic fields cause the membrane 9 to be deflected away from the coil which, in turn, results in a rather intense shock wave in the liquid of cavity 2. The shock wave propagates toward a center on account of the spherical calotta shaped configuration of the membrane 9 and of the coil 12. The shock wave within the cavity, basically, converges towards the cover 3 through the interface 6, and into the composite focal point 20 of the system, being essentially the focus of the spherical calotta shaped surfaces 13 and 11. The focal point 20 is situated in a kidney stone identified by numeral 20, the kidney is identified by numeral 18. Repeated sequences of shock waves will comminute the kidney stone, i.e. will break it up into grit or powder to be discharged by natural process.

This being the general operation, it should be mentioned that the capacitor 16 and the spark gap 17 can be replaced by other suitable devices for the production of an electric current, particularly an electric current pulse. There are other types of controlled pulse generators available, particularly of the type which can produce pulses at a relatively high repetition rate. FIG. 1, moreover, illustrates the axis 25 being a center line that runs through the center of the spherical calotta shaped face 11 and 13, on one hand, and the focal point 20 on the other hand. Reference numeral 26 essentially denotes the surface of a cone with an apex in focal point 20 and extending more or less from the fringe or fringe near areas of the membrane 9.

FIG. 1 shows also a density distribution pattern in the wire-conductor 12. The central portion of the spiral coil 12 has, as far as radial distance of adjacent loops is concerned, a more densely packed configuration near the center than near the outside, i.e. near that zone where the cone 26 intercepts the coil pattern. In other words, the distance of the windings from each other in radial direction gradually increases from the inside to the outside. This non-uniformity in a coil distribution causes a weakening of the pressure amplitude contour from points where the axis 25 intersects the membrane 9 towards more radially outwardly situated locations, i.e. towards the fringes where the membrane and the insulating foil are clamped in-between the housing parts 1a and 1b.

Figure 2:
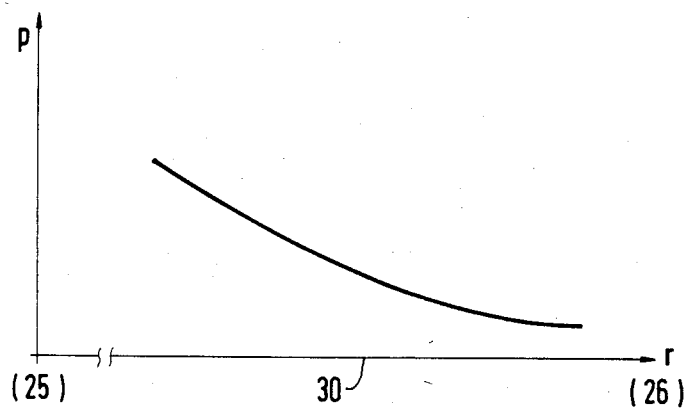
FIG. 2 illustrates a diagram plotting the pressure amplitude of shock waves in relation to the radial distance from the systems axis of the device shown in FIG. 1.

The decrease in amplitude of the shock wave as produced is depicted by way of example in FIG. 2. The diagram shown in FIG. 2 plots on the abscissa the radial distance "r" from the axis 25 and pertains, for example, to a shock wave, generated by means of the device shown in FIG. 1. The ordinate of the diagram represents the peak pressure amplitudes 31 of the shock wave as produced. Not the entire distribution 31 has been shown but only the fringe near or outermost zones of the shock waves are of interest, and this outer range 30 is shown accordingly. The restriction of the illustration to the outer zone is represented by the interruption of the abscissa through two wavy lines.

This outer zone or area or range 30 corresponds approximately to the fringe zone 26 in FIG. 1 while the axis 25 of FIG. 1 corresponds to the zero point in the diagram of FIG. 2. However, there are various comments to be made with regard to FIG. 2 that could be deemed applicable to the entire shock wave distribution over the various radial zones.

Curve 31, particularly in FIG. 2, shows that with increasing distance from the center (axis 25) the pressure amplitude drops, as was mentioned generally and qualitatively in connection with the description of FIG. 1. There is no inherent necessity that the curve 31 depicts a gradual decline, rather a stepwise drop, is within the scope of the possibility corresponding approximately to a stepwise increase in coil spacing, from the center toward the outside. Whatever the contour as far as pressure distribution is concerned, and local variants thereof, clearly should be developed ultimately by empirical tests, possibly to be combined with preliminary calculations.

It is pointed out that the invention basically deals with what could be called a parasitic effect which is, of course, subject to numerous influences and involves a plurality of different and different type of fringe effects that may vary with even minute construction variations as far as the fringe or outer zone of the system is concerned. the inventive principle is to provide for a reduction in the peak amplitude of the shock wave as it is produced at the generator area, the reduction to occur in radial outer direction. The rate of decline and the details of that decline, including possibly a stepwise reduction in pulse peak amplitude, is a matter of empirical adaptation to the existing conditions. Essential is that by this reduction in pressure amplitude, little or no fringe defraction waves, and therefore, no negative pressure pulse is produced, while on the other hand, the contour of the entire shock wave, including its temporal aspect, is improved, towards avoiding undesired fringe and side effects. The avoidance of negative pressure pulses avoids, for example, tissue damage in the kidney in which the concrement is located. A better controlled configuration of the shock wave as produced, on the other hand, is effective in a greater concentration of energy for and in the destruction of the concrement, such as a kidney stone.

Figure 3:
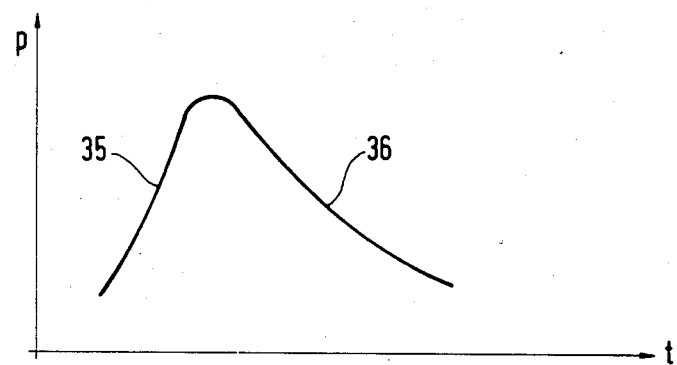
FIG. 3 is a timing diagram for such pressure pulses.

The pressure amplitude reduction as per FIG. 2 reduces, as stated, the production of negative pressure pulses, and therefore avoids damage to tissue. These effects can be increased significantly through a temporal control of the current that is fed to the coil 12. The temporal control of that pulse has at its aim the attainment of a particular pressure contour in time. FIG. 3 illustrates a particularly advantageous temporal shock pulse pressure distribution. The curve includes an amplitude rise segment 35 and a peak followed by a pressure drop 36. There is a certain asymmetry involved in that the rise 35 occurs steeper than the drop 36. This, however, is by way of example only, and for reasons above the specific circumstances may require optimization towards a different relationship between rise and decline. However, from a general point of view, it is believed that a very rapid pressure increase, followed by a slower decline, is always of advantage. It is only the relationship between the steepness of the two portions that varies, but it is not believed that a gradual increase followed by a steep decline will offer a comparable advantage though in odd cases such a possibility should not be excluded. The optimum contour of the pressure distribution in time will again be ascertained by way of experiment and also be based on calculations. Also, it should be considered that different types of pulse generations, i.e. not just a capacitor-spark gap discharge but other forms of pulse generation may require different considerations as far as the formation of the desired pressure contour is concerned.

Figure 4:
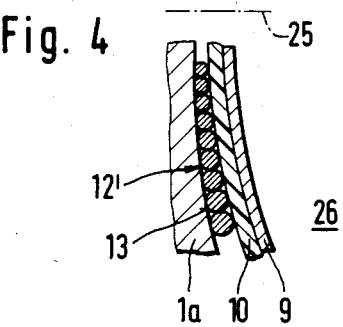
FIG. 4 is a detail of a certain portion of the device shown in FIG. 1.

A particular spatial pressure distribution is obtained by operation of the reduction in winding density of the conductor 12 as shown in FIG. 1. This, however, is not the only way of obtaining a reduction in pressure amplitude in radial outer direction. For example, FIG. 4 illustrates a modification of a portion of the device shown in FIG. 1. This modification involves the contour of certain parts. As in FIG. 1, there is a metal membrane 9 abutting an insulating foil 10 which, in turn, is physically coupled to the casing or housing part 1a through a conductor arrangement 12'. The inside of this housing part 1a is provided with a spherical calotta shaped abutment surface 13 as before. However, contrary to FIG. 1 a different kind of coil arrangement is used. FIG. 1, as will be recalled, uses a wire with the same cross-section and the radial density of the coils decreased, i.e. the radial spacing between adjoining wire loops increases. In FIG. 4, on the other hand, the wire thickness or diameter increases with radial distance from the system's axis. Particularly, then the wire in the vicinity of the axis 25 has a smaller diameter than wire portions being more radially remote from the axis 25. In other words, the wire thickness increases from the axis 25 in radial outer direction towards the cone 26. On the other hand, it has to be observed that the effect of this kind of increasing wire thickness is the same as obtained with a radially outwardly declining density in coil and increase in coil spacing for similar wire diameter.

In lieu of a round wire one could use a wire with a rectangular cross-section, i.e. a ribbon or strip of metal, whose thickness, however, increases so as to exhibit, as far as wire distribution in the coils is concerned, larger cross-section in more radial outer zones than near the center. Appropriate rolling of a metal strip can be instrumental here in obtaining a suitable flat conductor. On the other hand, the same concept shown in FIG. 1, can also be realized with a rectangular ribbon kind of conductor, namely an increase in coil density towards the radial outer zone. Finally, it can readily be seen that the features of FIG. 1 and FIG. 4 can be combined, the diameter of cross-sectional area thickness may increase as far as any coil is concerned in radial direction, and superimposed upon this distribution, the winding spacing may also increase in radial outer direction. The gaps inherently formed in-between adjacent loops as they are spaced farther apart, can be filled with insulating material, whereby, for example, in case of conductor strips, insulating strips of increasing thickness can be interposed. Again, a combination of the various features is available as wider conductors and larger spacing.

Figure 12:
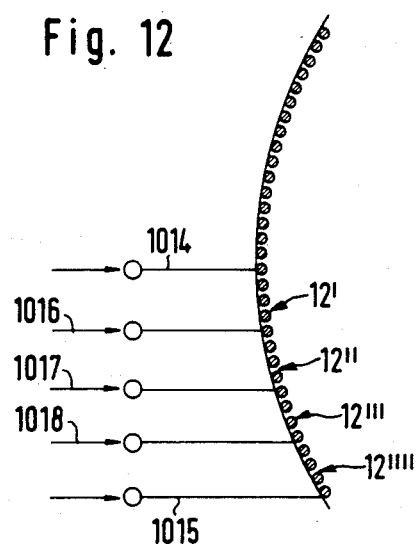
FIGS. 12 and 13 show embodiments of features of claim 28.
Figure 13:
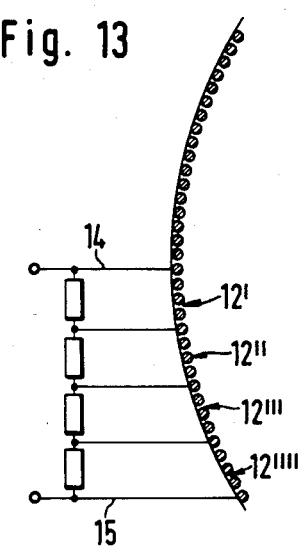

Another possibility of obtaining the radial pressure amplitude decline as per FIG. 2, is to be seen in using individual coils 12', 12'', 12''', 12'''', see FIG. 12 which are radially separated from each other, and these coils being of concentric arrangement are individually energized by separate electrical pulses 1014...1015, FIG. 12, each being controlled as to strength, rise time and decline etc. A concentric arrangement of these individual coils is for reasons for symmetry the most practical one, but for other purposes different kinds of arrangement on the surface 13 is feasible. Generally speaking, however, it was found to be of significant advantage to use concentrically arranged individual coils and to control the coils closer to the axis with a higher current than the current used for energizing coils with larger diameter. This, for example, is attainable in that the individual coils are controlled by separate devices producing the current pulses through suitable series and/or parallel circuits and/or through choice of different wire thicknesses and/or different circuit connections as far as different sections of the entire coil assembly is concerned. All these features offer parameters that can be used to modify the spatial temporal amplitude distribution of the pressure pulse. The different circuit connections involve separate connections of certain coil sections with separate terminals, series and/or parallel connections shunting see FIG. 13, adding of resistances, and controlling the current amplitude individually for each of these coil sections. The distance between the individual coils can also be made variable.

In case of a non-concentric arrangement of individual coils it was found to be of advantage to still provide in the inner part of the spherical calotta shaped surface 13 more windings of the respective coils than in outer more zones. The outer contour of these individual coils may have different configurations such as a star patterned, triangular, polygonal, and so forth. Superimposed upon these shape variations can be a varying wire thickness and individually selected control pulses for the individual coils. In the case of concentrical, as well as nonconcentrical arrangements, it is not necessary in principle to have the various windings of annular or circular configuration.

In case the cavity 2 as such is of truncated configuration as shown, for example, in my co-pending application Ser. No. 802,720, one can obtain a pressure amplitude decline in radial outward direction in accordance with FIG. 2 through modifications of the outer contour from a true truncated cone configuration that defines the transmission medium and fills the cavity 2. For example, the cone may widen in the direction towards cover 3 in a sense of a steeper apex angle, or the circularity of the contour of the cone in planes transversely to axis 25, may be modified. The attenuation produced by the wall of the cone maybe modified by providing sound damming material onto the surface of the truncated cone that fills the cavity 2 (i.e. the interface with the cone defining housing). In the case a solid truncated cone fills the cavity 2, one can alternatively cause the drop of the shock wave in radial direction in that beginning with the conical surface of this truncated cone pin-like elements project into the interior cavity to obtain some scattering of shock waves near the truncated cone's surface. Moreover, the various features and modifications discussed above, and concerning the coil configuration, i.e. the distribution of shock wave generation, can be combined with the features that involve shock wave propagation in the conical fringe zones of cavity 2. In other words, the variations in conical contour of the cavity, of course, permits in addition application of the various features outlined above with regard to cross-section, contour, coil spacing, distribution of the coils, and coil shape wire can all be used.

Figure 4A:
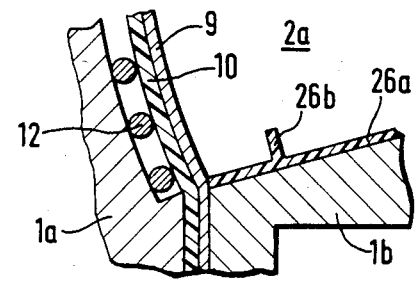
Figure 11:
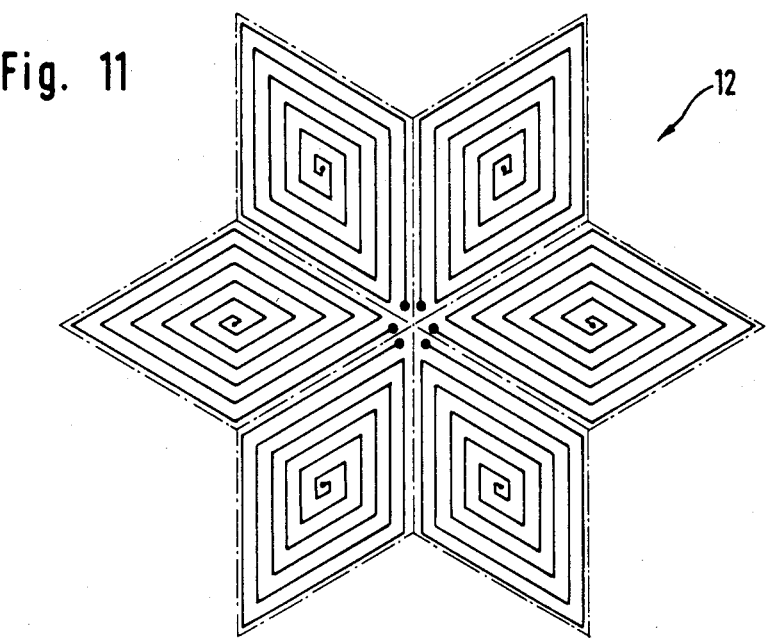
FIG. 11 shows an arrangement with a star-shaped coil, the star-shaped pattern is achieved by combining six rhombic coil arrangements.
Figure 15:
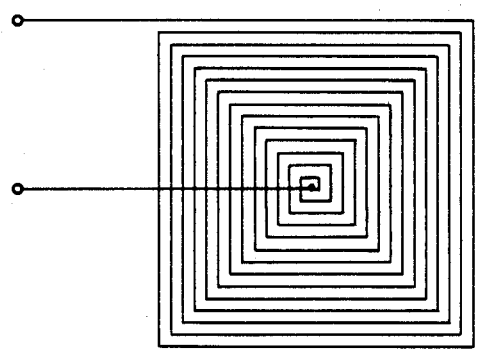
FIG. 15 shows a coil-figuration for an apparatus with a cone of quadratic cross section.

As was mentioned earlier, the pressure amplitude reduction as per FIG. 2 is obtainable by providing the conductor 12 in a star-shaped pattern (see FIG. 11). Analogously, it is possible in lieu, or in addition to the adaptation of the outer form of the conductors to modify other construction parts in the device shown in FIG. 1. For example, the cover 3 or the cavity filled with transmission medium 2a, particularly when contoured as a truncated cone, may in cross-section, i.e. in a plane transverse to the axis 25, be provided with a star-shaped or other non-circular configuration. Triangular, quadrilateral see FIG. 15, and other polygonal contours are possible, and that, in turn, can be combined with the other features mentioned above for pressure amplitude reduction. Also, suitable attenuating systems, such as layer 26a in FIG. 4a, absorbing and scatter elements 26b, for weakening shock waves near the fringe zones, can be used.

The invention was explained basically with reference to FIG. 1 and the device shown therein in general, but the invention can also be practiced in connection with devices which do not have a calotta shaped metal membrane, but use a planar metal membrane instead. It is, of course, now required to provide additionally for focusing of the planar shock wave produced by a flat metal membrane. Reflectors and lenses (acoustical ones) are now to be used for focusing the shock wave onto and into the concrement. Aside from this particular modification also various possibilities discussed above concerning pressure amplitude and reduction as per FIG. 2, can be used analogously, so that in all these instances practicing of the invention avoids the formation of negative pressure pulses, and therefore, damage to tissue.

From a different point of view, in lieu of coil-like conductors one could use other arrangements provided they produce shock waves. For example, point-shaped, line-shaped, curve-line shaped, areal, circular, or curved areal sources can be used. Shock waves produced in this manner and by such sources will then be focused through a suitable reflector and/or lens arrangement. The contour of the wave fronts will, in addition, be modified through intentional fringe scattering, absorption, or other ways of modifying existing waves in the outer zones. For purposes of contouring the waves, particularly focusing, one can use the same equipment for purposes of reducing the pressure amplitude in radial outer direction.

Figure 14:
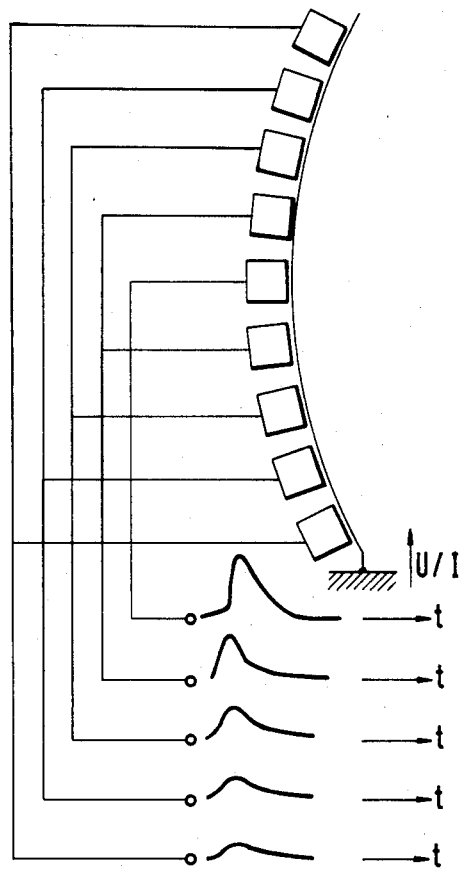
FIG. 14 shows an embodiment with features of claim 31.

As was mentioned earlier, for example, piezoelectric or magnetostrictive elements can be used as sources for shock waves see FIG. 14 or underwater spark discharge together with ellipsoidal focusing can be used. In each instance the source of the shock wave has a particular contour and modification and control, particularly of the amplitude of the shock wave generally, and more particularly in the fringe zones, will then be modified under utilization of such elements. For example, the control voltage for the various elements can be varied, the density and the arrangement of the various elements can be modified, and the size and shape of the various elements can be controlled analogously.

Using systems with direct and separate focusing devices, such as reflectors and/or mirrors, one may, in addition or in the alternative, control the amplitude of the shock waves such that the contour and size of the focusing arrangement is modified. Of particular advantage is here to provide, for example, the lense or reflector in a star-shaped, triangular, or polygonal contour or in a contour which can be regarded as fringed. In addition, the attenuation of the shock wave in the edge zone may be obtained through secondary attenuating absorbing and/or scattering features and elements.

One can, therefore, work under the assumption that all of these various systems have components and features which, in one form or another, relate to the production and/or focusing of shock waves, and the pressure amplitude can be modified as to spacial (radial) and temporal dimension, so that the local energization or excitation density and/or the local energization or excitation strength and/or shape and/or size of the source producing the shock wave or the shape and/or the size of the focusing device can be modified and/or any attenuation, absorption, or scattering of the shock wave can be changed as to radial distribution, varying during axial propagation.

Figure 5:
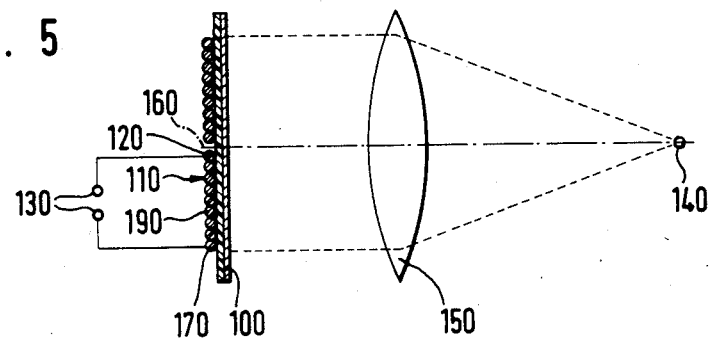
FIG. 5 is a schematic side-view of another embodiment of the present invention for practicing the best mode thereof under different operating conditions.
Figure 6:
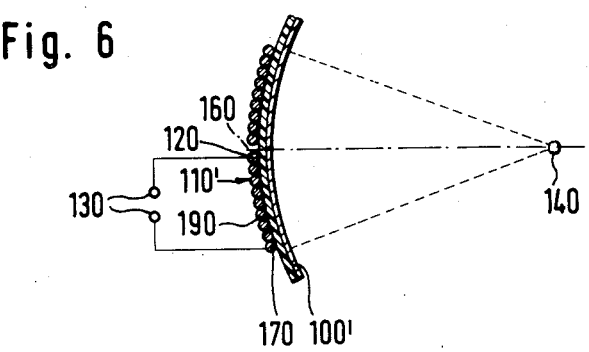
FIG. 6 is a schematic side-view of a spherical calotta shaped membrane-coil arrangement which can be used in the equipment of FIGS. 1 or 4.

The arrangement shown in FIGS. 5 and 6 is somewhat simplified and certain principle aspects are repeated here concerning electromagnetic devices for the contactfree comminution of concrements in the body of a living being. Here then a metal membrane 100 adjoins a coil 110 being comprised of a spirally shaped conductor 190. This conductor 190 has an inner connect point 120 and an outer connect point 170, both leading to the terminals 130. The center of the coil is identified by reference numeral 160 and corresponds essentially to the center of the essentially annular metal membrane 100.

As the coil 110 receives a current pulse through the terminal connection 130 the membrane 100 will be repelled from the coil 110. In view of special configurations of such devices additional elements, components, and bodies are provided on both sides of the membrane-coil arrangements 100-110, since particularly the membrane 100 is firmly clamped to the equipment, the shock waves produced by the membrane 100 in conjunction with the coil 110 will propagate in axis parallel relation, as a beam. Through appropriate devices 150 the beam is concentrated and focused onto the concrement 140 to be destroyed.

In case of FIG. 5, a planar metal membrane 100 adjoins a likewise planar coil 110. This means that on energizing the coil with a current pulse, a planar shock wave is produced. This planar shock wave is focused onto a point 140 by means of a lens 150. The concrement to be destroyed is located in that point 140. On the other hand, FIG. 6 shows a spherical calotta shaped membrane 100' adjoining analogously a spherical calotta shaped coil 110'. As a current pulse is fed to the coil 110', a shock wave is produced as described which, in this case, now without an extra focusing structure will be concentrated in point 140. Again, it can be said that a concrement will be situated in that point 140, to be destroyed.

Figure 7:
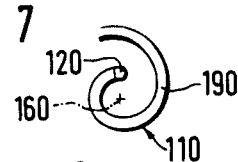
FIG. 7 is a schematic view of one of the coils as they are used in FIGS. 5 or 6.

Both FIGS. 5 and FIG. 6 reveal that the inner connect point 120 of the conductor 190 is not situated in this respective center 160 of either coil 110 or coil 110' but outside thereof. This particular aspect is shown in greater detail in FIG. 7. FIG. 7 in particular is a schematic front view of the coil 110 and is applicable either to FIG. 5 or to FIG. 6. The individual windings of the coil 110 (or 110') are separated for ease of illustration. Also, only the first winding of the coil 110 is shown, which has one end connected to the inner connect point 120 of the conductor 190, and loops directly around the coil center 160. It is important that the coil part 120, by means of which the coil is connected to further conductors, is situated outside of the coil center 160. In other words, no electric connection coincides with the center 160.

By means of the inventive arrangement, of providing particularly an off center beginning of 120 of the coil, one makes sure that the radius of curvature of the conductor 190 will not become too small, so that the insulation for the coil 110 will not crack. Also, sharp corners and edges of the conductor 190 are avoided, so that the breakthrough and/or short-circuiting danger is reduced, particularly when high current pulses are fed through the coil 110. Also, the reliability and use life of the coil is increased. Furthermore, the invention permits making of the coil in an automated fashion, and here the off center location of the point 120 is highly instrumental because no longer is it necessary to provide manual looping in and near the center of the coil.

Figure 8:
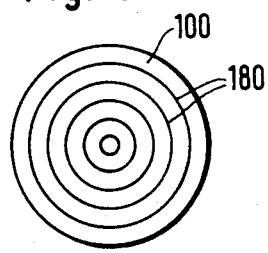
FIGS. 8, 9, and 10 are schematic views of different configurations for the metal membrane of the type used in FIGS. 5 or 6.
Figure 9:
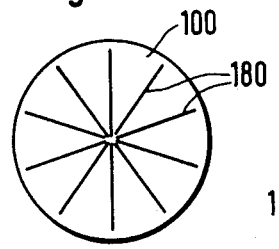
Figure 10:
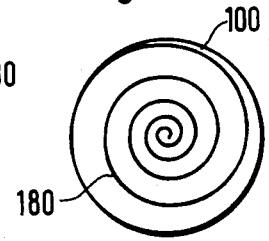

FIGS. 8, 9, and 10 show somewhat schematically three different configurations for the metal membrane 100 or 100′ as the case may be, and are, therefore, useful both in FIG. 5 and FIG. 6. In each of these instances, expansion grooves 180 are provided for the membranes. The grooves are arranged in different patterns in the various FIGS. 8, 9, and 10, providing in each instance a certain corrugation pattern. These corrugation grooves and ridges are arranged in an annulus in FIG. 8, radially in FIG. 9, and spirally in FIG. 10. In each case, of FIGS. 8, 9, and 10, the membrane is of a circular configuration.

The folds or grooves 180 and ridges in between in FIGS. 8, 9, and 10 can be made in various ways. For example, it is possible that wave-like folds are made in the various structure elements. Alternatively, one can establish different material thickness of the membrane 100 or 110 to thereby obtain these expansion folds 180. Particularly in the latter case, it is of advantage to provide the membrane 100 as a package of foils.

The folds 180 shown in FIGS. 8, 9, and 10, make it possible that as current is fed to the coil 110 (or 110′ or 12) a repulsion force is produced as far as the membrane 110 is concerned, i.e. membrane 110 is forced away from the coil 110. By operation of these grooves, one obtains, in fact, a very low mechanical load on membrane 100. As the membrane expands. Whereas, one can see that on one hand the membrane is protected through these folds from strong wear and excess loads and is, therefore, protected against rupture and fracture. On the other hand the formation of shock waves is enhanced by the particular contour and folds of and in the membrane 100 or 110. The use life of the membrane 100 is significantly increased by these folds 180 because in the past, generally speaking, the membrane 100 experiences maximum load in the center and the folds 180 reduce this load significantly in any of these examples.

Finally it should be mentioned that the invention is by no means limited to planar membrane and coil arrangements as per FIG. 5, but spherical calotta shaped arrangements as per FIG. 6 can also be used, and also the particular configuration of FIG. 1 is available. Also, it is possible to use rectangular cross-sections of wires in the arrangement shown in FIGS. 5 and 6, whereby particularly the spherical calotta shaped contour leads to the formation of placement for these wires. They are machined in an appropriate fashion. Also this aspect of the invention is likewise not limited to a circular cross-section of the conductors nor is a overall circular arrangement in loop form and configuration mandatory. Instead, star-shaped or polygonal arrangements can be used.

As stated in the introduction, the preferred field of employing the invention is the contactless comminution of kidney stones in the body of living beings, particularly of a human being, as was explained with reference to FIGS. 1 through 4.

The invention is not limited to the embodiments described above, but all changes and modifications thereof, not constituting departures from the spirit and scope of the invention, are intended to be included.

I claim:

1. Method for contactfree comminution of a concrement in the body of a living being, including the steps of generating shock waves and focusing the shock waves as generated in a focal area located in a concrement, there being an axis of rotational symmetry regarding the shock wave generation and on which said concrement is located, the improvement of reducing a pressure drop in the focal area, by providing the steps of:
   controlling in radial direction in relation to the axis, the energization distribution for the production of pressure shock waves such that the shock wave pressure amplitude generated at a given point in time decreases with radial distance from said axis; and
   temporarily controlling the generation of the shock waves such that the amplitudes rise steeply at first and decay relatively slowly after having passed through a maximum.

2. Method as in claim 1 said controlling step, including the step of varying the density of shock wave generation with distance from said axis.

3. Apparatus for contact free comminution of concrements in the body of living being, including means for generating shock waves, and means for focusing said shock waves along an axis and into a concrement to be comminuted, the improvement of, first means for controlling the means for generating as to an energization distribution in a radial distance from the axis, wherein so that the amplitude of the shock waves declines with the radial distance from said axis; and
   second means for controlling the temporal generation of the shock waves so that the shock waves have a steep rise time followed by a more gradual decay.

4. Apparatus as in claim 3 said generating means including calotta-spherically shaped energization means abutting an acoustic transmission medium such that upon energization of the generating means shock waves are directly produced in said transmission medium at the interface between the transmission medium and the means for generating, said first means being included in the generating means for obtaining a distribution variation of energization in said radial distance.

5. Apparatus as in claim 4, said generating means including energization means including coil means, said coil means having a coil winding density decreasing with said radial distance from the axis.

6. Apparatus as in claim 5, said coil means being arranged on a spherical-calotta shaped surface.

7. Apparatus as in claim 5, and said generating means including a membrane.

8. Apparatus as in claim 7, said membrane being provided with corrugation-like folds.

9. Apparatus as in claim 8, said folds being arranged in an annulus.

10. Apparatus as in claim 8, said folds being radially arranged.

11. Apparatus as in claim 8, said folds being spirally arranged.

12. Apparatus as in claim 8, said membrane being made of a package of foils.

13. Apparatus as in claim 4, said energization means including electrical conductor means distributed over a calotta-shaped surface.

14. Apparatus as in claim 9, wherein said conductor means is such that the membrane impedance increases with radial distance.

15. Apparatus as in claim 9, wherein the spacing inbetween the conductors increases with radial distance from said axis.

16. Apparatus as in claim 4, wherein said control means provide for attenuation that increases radially from said axis.

17. Apparatus as in claim 3, said means for generating including a metallic membrane interfacing a transmission medium being forced against the membrane, an insulating layer on the membrane facing away from the transmission medium, a flat spirally arranged conductor on the insulating layer having a loop winding density that decreases outwardly from an inner center of the spiral.

18. Apparatus as in claim 17, said membrane, said insulating layer, and the overall configuration of the conductor delineating a spherical calotta.

19. Apparatus as in claim 18, including a source for electrical pulses connected to said conductor.

20. Apparatus as in claim 3, wherein said means for generating shock waves includes a metal membrane abutting a relatively pressurized transmission medium for shock waves interfacing with that membrane for obtaining the generation of shock waves all along said interface on deflection of the membrane, an insulating layer on the membrane at a side facing away from said medium, a spirally arranged conductor arrangement on top of said insulating layer and having a cross-section that increases with distance from the center of the spiral.

21. Apparatus as in claim 20, said membrane, said conductor arrangement, and said insulating layer being spherically calotta shaped.

22. Apparatus as in claim 13 wherein the conductor means loops around a center in several windings.

23. Apparatus as in claim 13 wherein the conductor loops are non-circular, e.g. polygonal, spirally or star shaped.

24. Apparatus as in claim 13 wherein the conductor loops comprise a plurality of individual coils.

25. Apparatus as in claim 24 including individual pulse sources for the coils.

26. Apparatus as in claim 3, said shock wave generating means including membrane means and energizable means adjacent to the membrane for causing the membrane to vibrate, the energizable means being effective at a declining intensity with radial distance from a center.

27. Apparatus as in claim 26, said energizable means being piezoelectric.

28. Apparatus as in claim 26, said energizable means being electromagnetic.

29. Apparatus as in claim 26, said energizable means being magnetostrictive.

* * * * *